United States Patent [19]

Choi et al.

[11] Patent Number: 5,414,101
[45] Date of Patent: May 9, 1995

[54] PREPARATION OF HYDRIDOCARBONYL TRIS (TRIORGANOPHOSPHORUS) RHODIUM COMPOUNDS

[75] Inventors: Jung U. Choi; Sang M. Lee; Seong M. Jung, all of Daejeon, Rep. of Korea

[73] Assignee: Lucky, Ltd., Seoul, Rep. of Korea

[21] Appl. No.: 245,659

[22] Filed: May 18, 1994

[30] Foreign Application Priority Data

Oct. 20, 1993 [KR] Rep. of Korea .................... 93-22084

[51] Int. Cl.⁶ .............................................. C07F 15/00
[52] U.S. Cl. ..................................................... 556/136
[58] Field of Search ......................................... 556/136

[56] References Cited

U.S. PATENT DOCUMENTS 4,363,764 12/1982 Billig et al. ...................... 260/429 R
4,446,074 5/1984 Jamerson et al. ............... 260/429 R

*Primary Examiner*—José G. Dees
*Assistant Examiner*—Porfirio Nazario-Gonzales
*Attorney, Agent, or Firm*—Birch, Stewart, Kolasch & Birch

[57] ABSTRACT

Process for the preparation of hydridocarbonyl tris (triorganophosphorus) rhodium compounds from a concentrated hydroformylation reaction mixture.

15 Claims, No Drawings

PREPARATION OF HYDRIDOCARBONYL TRIS (TRIORGANOPHOSPHORUS) RHODIUM COMPOUNDS

FIELD OF THE INVENTION

This invention relates to the direct preparation of hydroformylation catalyst complex from rhodium complex concentrates which are derived from spent hydroformlation reaction mixtures containing a partially deactivated rhodium complex catalyst and triphenylphosphine.

BACKGROUND OF THE INVENTION

This invention pertains to the direct preparation of hydridocarbonyl tris (triorganophosphorus)rhodium complex from a concentrate residue which is derived from a spent hydroformylation reaction medium containing deactivated rhodium complex catalyst. More specifically, this invention pertains to the direct preparation of hydridocarbonyl tris (triorganophosphorus) rhodium in high yields from rhodium complex concentrates which are treated with an oxidant and by the following three steps of:

i) rhodium-carbonyl complex synthesis
ii) preparing the hydridocarbonyl tris (triorganophosphorus) rhodium complex
iii) post reaction with carbon monoxide and hydrogen Moreover, this process is distinguished by driect preparation of hydridocarbonyl tris (triorganophosphorus) rhodium in a one-phase organic reaction according to the above described steps without using halogen compounds and product separation in each step.

Hydridocarbonyl tris (triorganophosphorus) rhodium complex can be used as a catalyst in processes such as a hydrogen atom exchange reaction, isomerization, carbonylation and hydroformylation of olefins. Particularly it has excellent catalytic activity and selectivity in hydorformylation of olefins, and thus widely used as commercial processes.

There are several methods for the preparation of hydridocarbonyl tris (triorganophosphorus) rhodium complex.

In general it can be prepared from rhodium trichlorohydrate ($RhCl_3.3H_2O$), halocarbonyl bis (triorganophosphorus) rhodium and spent rhodium catalyst from hydroformylation distillate residue as a starting material.

Halocarbonyl bis (triorganophosphorus) rhodium as a starting material and hydrazine reduction method under ethanol solvent was disclosed in J. Amer. Chem. Soc., 85, 3500, 1963. Chem. Commun., 305, 1967 discloses that chlorocarbonyl bis (triphenylphosphine) rhodium complex was prepared by reacting with sodium tetrahydridoborate ($NaBH_4$) or a triethyl amine and hydrogen reaction under an ethanol solvent which contains excessive triphenylphosphine. It is also known in Inorg, Synth, 28, 81, 1990 that rhodium trichlorohydrate is converted by reaction with KOH, HCHO under ethanol solvent which contains triphenylphosphine. The yield of this reaction was 95%.

However, the preparation of hydridocarbonyl tris (triorganophosphorus) rhodium from rhodium complex, derived from a spent hydroformylation medium, is much more difficult than above preparation methods which use pure chemical grade. Furthermore, such rhodium complex, deactivated through various routes during hydroformylation reaction, may cause more difficulty in converting to hydridocarbonyl tris (triorganophosphorus) rhodium.

EP 0, 055, 487 describes the preparation of hydridocarbonyl tris (triorganophosphorus) rhodium by converting halocarbonyl bis (triorganophosphorus) rhodium through hydrogenation with sodium tetrahydroborate ($NaBH_4$). In this process halocarbonyl tris (triorganophosphorus) rhodium was prepared by reacting a hydroformylation reaction medium with HCl and DMF. The reaction yield was 86.6%.

U.S. Pat. No. 4,446,074 discloses the synthesis of hydridocarbonyl tris (triorganophosphorus) rhodium by reacting a hydroformylation reaction medium and KOH under ethanol solvent and subsequent treatment with syngas. However, a low recovery yield, 48%, was observed in this process. U.S. Pat. No. 4,113,754 describes the preparation process of hydridocarbonyl tris (triorganophosphine) rhodium from chlorocarbonyl bis (triorganophosphine) rhodium which was prepared from a hexachlororodate solution, tertiary phosphine, and carbonmonoxide. In this process the spent hydroformylation medium was treated with mineralic acid and peroxide compounds containing oxygen. Subsequently, the obtained water soluble rhodium salts and rhodium complex can be recovered by passing an aqueous solution in cation exchange resin. Hexachlorodate solution can be isolated by employing a hydrogen chloride aqueous solution. However, this process requires an aqueous phase and needs excessive mineralic acid and hydrogen chloride aqueous solution.

SUMMARY OF THE INVENTION

This invention is based on the discovery that a hydridocarbonyl tris (triorganophosphorus) rhodium complex can be prepared from a rhodium compound, which is contained in a hydroformylation reaction medium, by converting the deactivated rhodium complex catalyst in high yields to said hydridocarbonyl tris (triorganophosphorus) rhodium complex.

Thus, the invention provides an organic one-phase process for recovering the hydridocarbonyl tris (triorganophosphorus) rhodium directly from a hydroformylation reaction medium.

In the inventive method the deactivated rhodium complex catalyst is converted into a rhodium carbonyl compound and directly reacted with an alkali metal hydroxide, formaldehyde, a triorganophosphorus compound (as ligand) in hydroxyl containing solvent to produce said hydridocarbonyl tris (triorganophosphorus) rhodium compounds. In this stage, this compound is relatively unstable. Thus subsequent treatment, with carbon monoxide and hydrogen gas, provides high yields of said hydridocarbonyl tris (triorganophosphorus) rhodium compound.

The process of this invention as explained more fully below.

DETAILED DESCRIPTION OF THE INVENTION

This invention reveals that hydridocarbonyl tris (triorganophosphorus) rhodium can be prepared by an organic one-phase process from a rhodium complex which is contained in a hydorformylation reaction medium. The hydroformylation reaction is a well-known commercial process, which is catalytic method for the conversion of an olefin with carbon monoxide and hydrogen into an aldehyde product having one carbon more than the starting olefin. As pointed out in the above, the rhodium complex catalyst loses its original activity during the hydroformylation reaction. The extent of deactivation of the catalyst depends on the reaction time and condition. The partially deactivated rhodium complex catalyst, as well as its hydroformylation reaction medium, will be concentrated according to the method of vaccum distillation. The distilled residue of this process is generally referred as a spent hydroformylation reaction medium. The spent hydroformylation reaction mediums employed in this invention are those that contain partially deactivated rhodium complex catalyst, aldehyde products, higher boiling aldehyde condensation by-products and free triorganophosphorus compounds. It is more preferable to have a low content of lower boiling aldehydes in the spent hydroformylation reaction medium as a starting material of this invention. This is due to the solubility of hydridocarbonyl (triorganophosphorus) rhodium in lower boiling aldehydes.

The concentration of rhodium in a hydroformylation reaction distilled residue which is employed in this invention is preferably 1000~50000 ppm, more preferably 1500~30000 ppm. In the case of a rhodium concentration lower than 1500 ppm, a larger reaction vessel and repeated operation will be required in order to treat a hydroformylation reaction distilled residue which is derived on a commercial scale. When it is higher than 30000 ppm, the same will cause a rhodium cluster formation during distillation precess and thus making more difficult in recovery process.

The content of triorganophosphorus compound which is contained in distilled residue in this invention can be effective at about 1~40 wt %, more preferably at 1-30 wt %.

The hydroformylation reaction distilled residue which is employed in this invention should be reacted with an oxidizing agent like oxygen or air at a reaction temperature of from about 60° C. to about 120° C. and at a pressure from about 1 atm to 10 atm before the recovery process begins. According to this oxidation, the partially deactivated rhodium complex is converted into an easily changeable form. It is still fully unknown that the structure is of deactivated rhodium complex which is derived from hydroformylation reaction. However, it is known that its activity can be partially restored by treating it with an oxidizing agent like oxygen or air, to thereby facilitate the recovery.

It is known that the diphenyl phosphido bridged rhodium cluster compound is formed during a hydroformylation reaction in the presense of a catalyst with a triphenyl phosphine ligand. Thus it is to be understood that when the phosphine bridge is oxidized with an oxydizing agent like oxygen or air, the same weakens the binding force between the rhodium and phosphine, and facilitates the reactivation or recovery. [I]

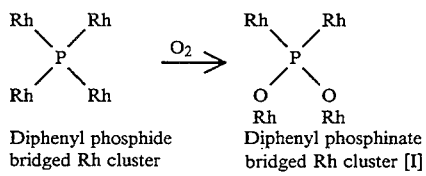

Diphenyl phosphide bridged Rh cluster

Diphenyl phosphinate bridged Rh cluster [I]

This invention relates to a process for an organic one-phase synthesis of hydridocarbonyl tris (triorganophosphorus) rhodium from a rhodium containing concentrate residue.

The preparation process consists of following three steps.

i) rhodium carbonyl complex synthesis step
ii) hydridocarbonyl tris (triorganophosphorus) rhodium synthesis step
iii) subsequent gas reaction with carbon monoxide and hydrogen The process of each step of this invention is explained more fully below.

The rhodium-carbonyl compound of this invention is prepared by reacting carbon monoxide and oxygen with a rhodium complex concentrate residue. The role of oxygen in this step facilitate the process of obtaining a rhodium carbonyl compound from a deactivated rhodium complex. In general, the ratio of partial pressure of carbon monoxide to oxygen employed in this invention may range from about 5:1 to about 30:1. It is proper that the total pressure of carbon monoxide and oxygen is from about 10 bar to about 100 bar. When the partial pressure ratio of carbon monoxide to oxygen is smaller than 5:1 it may cause a danger of explosion, and when it is greater than 30:1 it may decrease the effect of the oxygen. The reaction is conducted at temperatures from about 60° C. to 150° C., preferably from 80° C. to 120° C., and at a time of about 10 minutes to 5 hours. With the rhodium concentrate residue there can also be employed additional solvent which contains a hydroxyl group compound, when it is highly viscous. The reaction product of this step is a rhodium carbonyl compound, but the reaction process may further proceed, without separation of the rhodium carbonyl compound, and the synthesis for the hydrido carbonyl tris (triorganophosphorus) rhodium can take place in the same reactor.

The synthesis step of the hydridocarbonyl tris (trioganophosphorus) rhodium in this invention employs a hydroxyl group containing compound, a triorganophosphorus ligand in a rhodium carbonyl compound reaction mixture and and reacting the same with an alkali metal hydroxide and formaldehyde. The hydroxyl group contained compound is an alcohol which has a carbon number from 1 to 3 in this step. Illustrative examples of compound are methanol, ethanol, isopropanol etc. Ethanol is prefered of these. Exemplary of the alkali metal hydroxide are NaOH, KOH, LiOH, etc., which when employed can react with the hydroxyl group contained compound employed in this process to furnish the hydrogen of the desired hydridocarbonyl tris (triorganophosphorus) rhodium product. It can also convert the carbonyl group containing complex in the concentrate residue into hydroxyl compounds. Thus it is easy to recover the desired product due to a decrease of its solubility in the reaction mixture. On the other hand, the alkali metal hydroxide may convert the deactivated rhodium complex, which is strongly binded in the form of cluster, into an easily recoverable form of rhodium complex. Thus it provides an increase in hydridocarbonyl tris (triorganophosphorus) rhodium recovery.

The amount of alkali metal hydroxide which is employed in this invention may range from 1 to 40 times on the basis of rhodium moles, preferably 4~20 times.

The formaldehyde which is employed in this invention is a water free mixture with methanol. In general, the weight ratio of methanol:formaldehyde is from about 5:1 to about 1:1. The amount of formaldehyde varies according to the amount of concentrate residue and its rhodium concentration. In general, the amount of pure formaldehyde employable in this invention is preferably from 0.1 to 3 weight %. The formaldehyde is a source of carbonyl groups in the rhodium compound.

The triorganophosphorus ligand in this invention is described as having a general formula of $PX_3$ (Where in X=OPh, OR, R, Ph:Ph=Phenyl, R=alkyl). The most prefered triarylphosphine is triphenylphosphine. The amount of triorganophosphorus ligand employed in this invention can be varied according to the rhodium content in the concentrate residue as well as its solubility to the concentrate residue and the employed hydroxyl group containing compound. It should be employed greater than 3 times based on rhodium mole content, preferably from 3 to 30 mole times, more preferably from 3 to 30 mole times, most preferably from 4 to 20 mole times. The post treatment with according to carbon monoxide and hydrogen in this invention is based on the objective to obtain hydridocarbonyl tris (triorganophosphorus) rhodium in high yields. The rhodium complex which is unreacted during the hydridocarbonyl tris (triorganophosphorus) rhodium synthesis step is converted into the desired product in this step. The post treatment with carbon monoxide and hydrogen should be conducted first with carbon monoxide and then with hydrogen. Accordingly the hydridocarbonyl tris (triorganophosphorus) rhodium which is insoluble to the concentrate residue and the hydroxyl group containing compound, can be obtained in high yields. The treatment with carbon monoxide in this invention provide a source of carbonyl group in rhodium complex, which was unreacted in the previous step due to an insufficient carbon monoxide source.

The carbon monoxide employed in this step is carbon monoxide itself or a carbon monoxide containing gas. In general, a carbon monoxide contained gas is a synthesis gas comprising the ratio of carbon monoxide to hydrogen of from 1:5 to 5:1, preferably 1:1. The carbon monoxide containing gas treatment procedure being conducted at temperature of about 50° C. to 100° C., preferably from 55° C. to 70° C., and pressures of about 1 to 100 atm, preferably about 10 to 40 atm. The reaction time in this step requires from several minutes to several hours. In general, from 0.5 to 3 hours is sufficient. Finally, a stable hydridocarbonyl tris (triorganophosphorus) rhodium can be obtained according to a hydrogen treatment procedure. It is generally understood that hydridocarbonyl tris (triphenylphosphine) rhodium may take part in a reversible exchange reaction (reaction II) with a triorganophosphorus ligand and carbon monoxide under a carbon monoxide atmosphere.

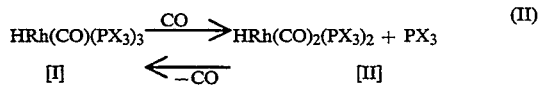

$$HRh(CO)(PX_3)_3 \underset{-CO}{\overset{CO}{\rightleftarrows}} HRh(CO)_2(PX_3)_2 + PX_3 \quad (II)$$
$$[I] \qquad\qquad\qquad [II]$$

It is also known that the obtained compound [II] may form a equilibrium according to the reaction III.

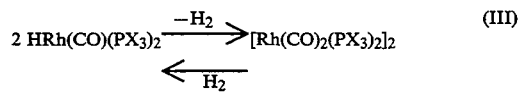

$$2 HRh(CO)(PX_3)_2 \underset{H_2}{\overset{-H_2}{\rightleftarrows}} [Rh(CO)_2(PX_3)_2]_2 \quad (III)$$

Thus the recovery of hydridocarbonyl tris (triorganophosphorus) rhodium is decreased due to the formation of a rhodium dimer compound which is soluble in the hydroxyl group contained compound and concentrate residue. In order to obtain a hydridocarbonyl tris (triorganophosphorus) rhodium in high yields, it should therefore be treated with hydrogen under excess triorganophosphorus ligand. The hydrogen treatment procedure takes place at temperatures of about 50° C. to 100° C., preferably from 60° C. to 80° C., and pressures of about 1 to 100 atm. preparably 10 to 40 atm. The reaction time of the hydrogen treatment requires from several minutes to several hours. In general from 0.5 to 4 hours is sufficient.

As explained above this invention relates to the direct preparation of hydrido tris (triorganophosphorus) rhodium a from rhodium catalyst contained concentrate residue according to organic one-phase reaction. The deactivated rhodium catalyst is converted into a rhodium-carbonyl compound and this reaction mixture, without separation of the rhodium compound, is further reacted with a hydroxyl group contained compound, alkali metal hydroxide, formaldehyde, and a triorganophosphorus ligand. According to the final after treatment with carbon monoxide and hydrogen, the hydridocarbonyl tris (triorganophosphorus) rhodium can be obtained in high yields.

The following examples are illustrative of the present invention. The prepared hydridocarbonyl tris (triorganophosphorus) rhodium of following examples was confirmed by infrared spectrometry (IR) and X-ray diffraction (XRD). The rhodium content in hydridocarbonyl tris (triorganophosphorus) rhodium complex was determined by inductive coupled plasma (ICP).

EXAMPLE 1

A spent hydroformylation reaction medium obtained from a continuous hydroformylation process of propylene with carbon monoxide and hydrogen to produce butyraldehyde in the presense of rhodium complex catalyst and free triphenyl phosphine ligand, whose activity had declined, was concentrated by using a wiped film evaporator. The rhodium complex concentrate distillation residue which was found to contain about 20,000 ppm rhodium was aerated at a temperature of 90° C. for 24 hours. After the aeration, the aerated concentrate residue was analyzed by gas chromatograph. All the of triphenylphosphine was converted into triphenylphosphine oxide during this aeration. A reaction mixture of about 130 g of said aerated distillation residue and 350 g of ethanol was prepared and added to a 2 l autoclave. The autoclave was charged with about 5.4 atm. of oxygen and additional carbon monoxide about to 26.5 atm. under room temperature. The reaction mixture was heated at 100° C. for 3 hours and cooled down to room temperature and then vented to one atmosphere. About 40 grams of triphenylphosphine was added to said reaction mixture and heated to reflux condition (80° C.).

After addition of about 8 grams of potassium hydroxide and about 10 ml of a formaldehye/methanol solution (1:1 wt. %), the reaction was maintained for 3 hours and then cooled down to room temperature. Then the reaction mixture was pressurized to 26 atm. with carbon monoxide and heated to 60° C. for 2 hours and then vented to the atmosphere. Subsequently, the hydrogen was charged to 24 atm. and heated to 70° C. for 2 hours and then cooled down to room temperature. After filtration of the reaction mixture, the obtained yellow solid was dried in a vaccum dryer. The recovered yellow solid product was confirmed by intrared spectrometry (IR) and X-ray diffration (XRD) and proved to indeed be hydridocarbonyl tris (triphenyl phosphine) rhodium. The amount of rhodium recovered as solid HRh(CO)(PPh3)3 corresponded to a yield of 95.5% by the result of ion coupled plasma (ICP) analysis.

EXAMPLE 2

A rhodium complex concentrate residue produced as described in Example 1 and containing about 4,200 ppm rhodium was aerated at a temperature of 90° C. for 15 hours. About 50 g of said aerated concentrate residue was added to a 300 ml autoclave. The solution was then charged with about 5.4 atm of oxygen and additional carbon monoxide added to about 21.1 atm. The reaction mixture was heated to 100° C. for 4 hours and cooled down to room temperature and then vented to one atmosphere. About 10 grams of triphenylphosphine and 70 grams of ethanol was added to said reaction mixture and heated up to a reflux condition. Under this condition, 2 grams of KOH, 10 ml of HCHO/MeOH solution (1:1 wt %) was added to said reaction mixture and reacted for 3 hours. The solution was then pressurized to 26 atm with carbon monoxide and reacted at 60° C. for 2 hours and then vented to atmosphere. Subsequently the hydrogen was charged into said reaction mixture to 24 atm and reacted at 70° C. for 2 hours and then vented to the atmosphere. The suspension was filtered and the obtained yellow solid was dried in a vaccum dryer. The obtained yellow solid product was confirmed by infrared spectrometry (IR) and X-ray diffraction (XRD) and proved to indeed be hydridocarbonyl tris (triphenylphosphine) rhodium. The amount of rhodium recovered as solid HRh(CO)(PPh3)3 coresponded to a yield of 95.2% by the result of ion coupled plasma (ICP) analysis.

EXAMPLE 3

The procedures of Example 2 were repeated, except the gas reaction with oxygen was at about 2.7 atm, and additional carbon monoxide totaled about 26.5 atm. The obtained yellow solid prduct was confirmed by IR and XRD and proved to indeed be hydridocarbonyl tris (triphenylphosphine) rhodium. The recovered rhodium was found to a yield of 91.8% by the analysis of solid product and filtrate.

EXAMPLE 4

A rhodium complex concentrate residue produced as described in Example 1, containing about 4,200 ppm rhodium was aerated at a temperature of 90° C. for 15 hours. About 300 g of said aerated concentrate residue and 300 g of ethanol was prepared and added to a 2 l autoclave. The autoclave was charged with about 5.4 atm of oxygen and additional carbon monoxide totaled 26.5 atm. The reaction mixture was stirred and heated to 100° C. for 2.5 hours and then vented to the atmosphere. About 40 grams of triphenylphosphine was added to said reaction mixture and heated to reflux conditions (80° C.). After addition of about 10 grams of potassium hydroxide and about 10 ml of a formaldehyde/methanol solution (1:1 wt %), the reaction was allowed to proceed for 3 hours, and then the mixture cooled down to room temperature. Then the reaction mixture was pressurized to 26 atm with carbon monoxide and heated at 60° C. for 2 hours and then vented to the atmosphere. Subsequently, hydrogen was charged to 24 atm and reacted at 70° C. for 2 hours. The suspension was filtered and the obtained yellow solid was dried in a vaccum dryer. The recovered yellow solid product was confirmed by IR and XRD and proved to be hydridocarbonyl tris (triphenylphosphine) rhodium. The recovered rhodium was found to a yield of 94.1% by the analysis of solid product and filtrate. The invention has been described in detail with particular example to preferred embodiments thereof but it will be understood that variations and modifications may be effected within the sprit and scope of the invention.

We claim:

1. A process for the direct preparation of a hydridocarbonyl tris (triorganophosphorus) rhodium according to a one-phase organic reaction from a concentrate residue containing a deactivated rhodium complex, which is derived from a spent hydroformylation reaction medium containing the deactivated rhodium complex catalyst, the process comprising the following steps:
   i) oxidizing the concentrate residue with an appropriate oxidant;
   ii) synthesizing a rhodium carbonyl complex from the deactivated rhodium complex under a carbon monoxide and oxygen gas mixture atmosphere;
   iii) preparing the hydridocarbonyl tris (triorganophosphorus) rhodium complex by directly reacting the rhodium carbonyl complex with a hydroxyl group containing compound, an alkali metal hydroxide, formaldehyde and a triorganophosphorus ligand; and
   iv) reacting remaining rhodium carbonyl complex with carbon monoxide, and reacting the hydridocarbonyl tris(triorganophosphorus) complex with hydrogen.

2. A process according to claim 1, wherein the oxidant is air or oxygen, and step i) is carried out at a temperature from about 60° C. to about 120° C. and a pressure of from about 1 to 10 atm.

3. A process according to claim 1, wherein the rhodium concentration in the concentrate residue is from about from 1,500 ppm to 30,000 ppm.

4. A process according to claim 1, wherein the rhodium carbonyl compound is prepared at a partial pressure ratio of carbon monoxide to oxygen of from about 5:1 to about 30:1, and a total reaction pressure of about 10 to 100 atm.

5. A process according to claim 4, wherein the rhodium carbonyl compound is prepared at a temperature of from about 80° C. to about 120° C.

6. A process according to claim 1, wherein the hydroxyl group containing compound is ethanol.

7. A process according to claim 6, wherein the amount of the hydroxyl group containing compound employed is about 1 to 10 weight times that of the concentrate residue.

8. A process according to claim 1, wherein the alkali metal hydroxide is potassium hydroxide.

9. A process according to claim 8, wherein the alkali metal hydroxide is present in an amount of about 4 to 20 mole times that of the total rhodium moles present in said concentrate residue.

10. A process according to claim 1, wherein the formaldehyde consists essentially of a water free methanol/formaldehyde mixture which has a ratio from about 5:1 to 1:1, and wherein the mixture is employed in an amount from about 0.1 to 10 weight %, on the basis of said concentrate residue.

11. A process according to claim 1, wherein the triorganophosphorus ligand is triphenylphosphine or triphenylphosphite.

12. A process according to claim 11, wherein the amount of the triorganophosphorus ligand is from about 4 to 20 mole times that of the total rhodium moles present in said concentrate residue.

13. A process according to claim 1, wherein step iv) comprises reacting with hydrogen, after reacting with carbon monoxide.

14. A process according to claim 13, wherein the carbon monoxide reaction is conducted at a temperature of from 55° C. to 70° C. and a pressure of about 1 to 100 atm.

15. A process according to claim 13, wherein the hydrogen reaction is conducted at a temperature of from about 60° C. to 80° C. and a pressure of about 1 to 100 atm.

* * * * *